United States Patent [19]

Chambers et al.

[11] Patent Number: 5,451,582

[45] Date of Patent: Sep. 19, 1995

[54] BENZODIAZEPINE DERIVATIVES, COMPOSITIONS CONTAINING THEM AND THEIR USE IN THERAPY

[75] Inventors: Mark S. Chambers, Watford; Victor G. Matassa, Furneux Pelham; Stephen R. Fletcher, Nr. Bishops Stortford, all of England

[73] Assignee: Merck Sharp & Dohme Ltd., Hoddesdon, England

[21] Appl. No.: 16,646

[22] Filed: Feb. 12, 1993

[30] Foreign Application Priority Data

Feb. 21, 1992 [GB] United Kingdom ........... 9203790

[51] Int. Cl.$^6$ .................. C07D 243/24; A61K 31/55
[52] U.S. Cl. ..................................... 514/221; 540/509
[58] Field of Search ............. 514/221; 540/522, 504, 540/509

[56] References Cited

U.S. PATENT DOCUMENTS

| | | | |
|---|---|---|---|
| 4,820,834 | 4/1989 | Evans et al. | 540/504 |
| 5,010,076 | 4/1991 | Waldeck et al. | 514/221 |
| 5,175,159 | 12/1992 | Bock et al. | 540/509 |
| 5,302,591 | 4/1994 | Fletcher et al. | 540/509 |
| 5,360,802 | 11/1994 | Chambers et al. | 540/509 |

FOREIGN PATENT DOCUMENTS 167919 6/1985 European Pat. Off. .

OTHER PUBLICATIONS

Chemical Abstracts vol. 119(13): 139279s (1993).
Chemical Abstracts vol. 118(11): 101998s (1993).
Life, Sci. 30, 479 (1982), by J. E. Morley.
Br. J. Pharmacol, 105, pp. 8–10 (1992), by Singh, et al.
J. Med. Chem., 32, pp. 13–16 (1989), by M. Bock, et al.

*Primary Examiner*—Nicholas Rizzo
*Attorney, Agent, or Firm*—Robert J. North; Melvin Winokur; Joseph F. DiPrima

[57] ABSTRACT

Compounds of formula (I), and salts and prodrugs thereof

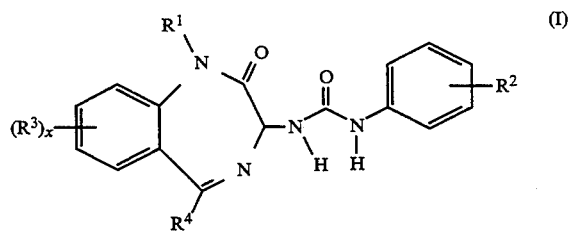

wherein:

$R^1$ is H, certain optionally substituted $C_{1-6}$alkyl, or $C_{3-7}$cycloalkyl;

$R^2$ is $(CH_2)_q$-tetrazolyl optionally substituted in the tetrazole ring by $C_{1-4}$alkyl, $(CH_2)_q$-imidazolyl (where q is 0, 1, 2 or 3), $CONHSO_2R^9$, $SO_2NHCOR^9$ (where $R^9$ is $C_{1-6}$alkyl, optionally substituted aryl or trifluoromethyl). $SO_2NHR^{10}$ (where $R^{10}$ is a nitrogen containing heterocycle), cyclopropyl or $(CH_2)$, $CO_2H$, where n is 1 or 2;

$R^3$ is $C_{1-6}$alkyl, halo or $NR^6R^7$;

$R^4$ is $C_{1-7}$ straight or branched chain alkyl; and x is 0, 1, 2 or 3;

are CCK and/or gastrin receptor antagonists. They and compositions thereof are useful in therapy.

10 Claims, No Drawings

BENZODIAZEPINE DERIVATIVES, COMPOSITIONS CONTAINING THEM AND THEIR USE IN THERAPY

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-$NH_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33 [1982] and references cited therein; J. A. Williams, *Biomed Res.* 3 107 [19829]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T.H. Moran et al., "Two brain cholecystokinin receptors: implications for behavioural actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, $\beta$-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. pharmacol.*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485 [1990]), thus having utility in inducing miosis for therapeutic purposes.

European patent application no. 0 167 919 discloses benzodiazepine CCK and gastrin antagonists substituted in the 3-position by, inter alia, a phenyl urea and at the 5-position by, inter alia, a $C_{1-4}$alkyl group. There is no suggestion of the phenyl urea substitution of the compounds of the present invention.

The present invention provides benzodiazepine compounds of formula (I)

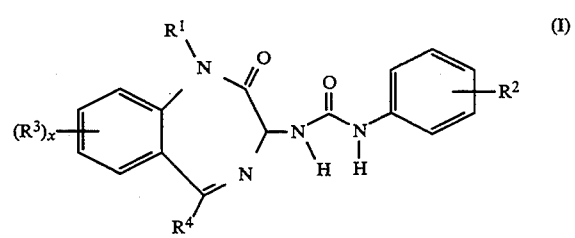

wherein:

$R^1$ represents H, $C_{1-6}$alkyl, $C_{3-7}$cycloalkyl, cyclopropylmethyl, $CH_2CO_2R^5$ (where $R^5$ is $C_{1-4}$alkyl) or a group $CH_2CONR^6R^7$ (where $R^6$ and $R^7$ each independently represent H or $C_{1-4}$alkyl, or $R^6$ and $R^7$ together form a chain $(CH_2)_p$ where p is 4 or 5);

$R^2$ represents $(CH_2)_q$-tetrazolyl optionally substituted in the tetrazole ring by $C_{1-4}$alkyl, $(CH_2)_q$-imidazolyl (where q is 0, 1, 2 or 3), $CONHSO_2R^9$, $SO_2NHCOR^9$ (where $R^9$ is $C_{1-6}$alkyl, optionally substituted aryl or trifluoromethyl), $SO_2NHR^{10}$ (where $R^{10}$ is a nitrogen containing heterocycle), cyclopropyl or $(CH_2)_nCO_2H$, where n is 1 or 2;

$R^3$ represents $C_{1-6}$alkyl, halo or $NR^{16}R^{17}$, where $R^{16}$ and $R^{17}$ each independently represent H or $C_{1-4}$alkyl, or $R^{16}$ and $R^{17}$ together form a chain $(CH_2)_r$ where r is 4 or 5;

$R^4$ represents $C_{1-7}$ straight or branched chain alkyl; x is 0, 1, 2 or 3;.
and salts and prodrugs thereof.

It will be appreciated that formula (I) is intended to embrace all possible isomers, including optical isomers, and mixtures thereof, including racemates.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

As used herein, unless otherwise stated, alkyl means linear or branched chain alkyl. Examples of suitable alkyl groups include methyl, ethyl, isopropyl and isobutyl groups.

When $R^1$ represents cycloalkyl, examples of suitable cycloalkyl groups include cyclopropyl, cyclopentyl and cyclohexyl groups, preferably cyclopropyl.

Halo includes fluoro, chloro, bromo and iodo. Preferably halo will be fluoro or chloro.

Unless otherwise stated, aryl means optionally substituted carbocyclic or heterocyclic aromatic groups, especially phenyl.

Heteroaryl means aromatic rings preferably having 5 or 6 ring atoms and containing at least one atom selected from O, S and a group $NR^{13}$, where $R^{13}$ is H or $C_{1-4}$ alkyl.

When $R^9$ is optionally substituted aryl, this will preferably be optionally substituted phenyl. Suitable substituents include $C_{1-4}$alkyl, $C_{1-4}$alkoxy, halo and trifluoromethyl. Preferred are compounds wherein $R^9$, is unsubstituted phenyl or phenyl substituted by $C_{1-4}$alkyl, for example, phenyl substituted by $C_{1-4}$alkyl, such as methyl, in the ortho position.

When $R^9$ is $C_{1-6}$alkyl, it will preferably represent $C_{1-4}$alkyl. Particularly preferred are methyl and isopropyl.

When $R^2$ is $SO_2NHR^{10}$, suitable values of $R^{10}$ include, for example, thiazole, thiadiazole and pyrazine.

Preferably $R^1$ is $C_{1-6}$alkyl, such as methyl, n-propyl or isobutyl.

Preferably $R^2$ is in the 3- or 4-position, more preferably the 3-position.

In one preferred group of compounds of formula (I), $R^2$ is tetrazolyl, more preferably 3-tetrazol-5-yl.

In a further preferred group of compounds of formula (I), $R^2$ is $CONHSO_2R^9$ or $SO_2NHCOR^9$, more preferably $CONHSO_2R^9$.

Suitable values for $R^9$ include methyl, ethyl, i-propyl, t-butyl, phenyl, o-tolyl and trifluoromethyl.

Suitable values for $R^3$ include methyl and dimethylamino.

Preferably x is 0 or 1, more preferably 0.

Suitably $R^4$ represents $C_{1-4}$alkyl, such as methyl, ethyl, i-propyl or t-butyl, preferably i-propyl or t-butyl.

One subgroup of compounds according to the invention is represented by compounds of formula (I) wherein $R^1$ represents $C_{1-6}$alkyl, $C_{3-7}$cycloalkyl, cyclopropylmethyl, $CH_2CO_2R^5$ or $CH_2CONR^6R^7$; $R^2$ represents $(CH_2)_q$-tetrazolyl wherein one of the N atoms is optionally substituted by methyl, $(CH_2)_q$-imidazolyl, $CONHSO_2R^9$, $SO_2NHCOR^9$, $SO_2NHR^{10}$, cyclopropyl or $(CH_2)_nCO_2H$; $R^3$ is $C_{1-6}$alkyl or halo; and x is 0 or 1.

A preferred subgroup of compounds according to the invention is represented by compounds of formula (IA), and salts and prodrugs thereof:

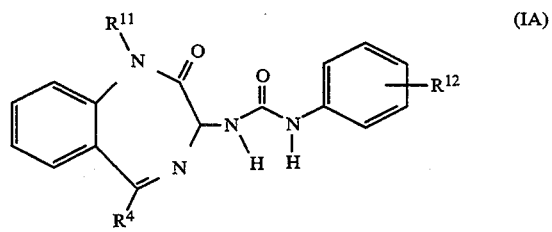

(IA)

wherein $R^{11}$ is $C_{1-6}$alkyl, preferably $C_{1-4}$alkyl;
$R^{12}$ is tetrazolyl, $CONHSO_2R^9$ or $SO_2NHCOR^9$, where $R^9$ is as previously defined, preferably tetrazolyl or $CONHSO_2R^9$; and
$R^4$ is as defined for formula (I), preferably $C_{1-4}$alkyl.

Preferred are compounds of formula (IA) wherein $R^{12}$ is in the 3-position of the phenyl ring.

Preferably the salts of the compounds of formula (I) are pharmaceutically acceptable, but non-pharmaceutically acceptable salts may be useful for the preparation of pharmaceutically acceptable salts, and are within the scope of the present invention. The pharmaceutically acceptable salts of the compounds of formula (I) include the conventional non-toxic salts or the quaternary ammonium salts of the compounds of formula (I). For example, such conventional non-toxic salts include basic salts, e.g. sodium and potassium salts.

The salts of the present invention can be synthesized from the compound of formula (I) which contain an acidic moiety by conventional chemical methods. Generally, the salts are prepared by reacting a compound of formula (I) with stoichiometric amounts or with an excess of the desired salt-forming inorganic or organic base in a suitable solvent or combination of solvents.

The present invention also encompasses a pharmaceutical composition comprising a compound of formula (I), or a salt or prodrug thereof, and a pharmaceutically acceptable carrier.

The compounds of formula (I) and their salts and prodrugs may be administered to animals, preferably to mammals, and most especially to a human subject either alone or, preferably, in combination with pharmaceutically acceptable carriers, optionally with known adjuvants, such as alum, in a pharmaceutical composition, according to standard pharmaceutical practice. The compounds can be administered orally, parenterally, including by intravenous, intramuscular, intraperitoneal or subcutaneous administration, or topically.

For oral use the selected compounds according to this invention may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients—such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastro-esophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression, such as depression resulting from organic disease, secondary to stress associated with personal loss or idiopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate-mediated, as well as anaesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occurring in association with iritis, ureitis and trauma.

The present invention therefore provides a compound of formula (I) or a salt or prodrug thereof for use in the preparation of a medicament for the treatment of a physiological disorder involving CCK and/or gastrin.

The present invention also provides a compound of formula (I), or a salt or prodrug thereof, for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing-analgesia, anaesthesia or loss of pain sensation, the effective dosage preferably ranges from about 100 ng/kg to about 1 mg/kg by intravenous administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared by processes analogous to those described in European patent specification No. 0284256. For example, a compound of formula (I) may be prepared by reaction of an intermediate of formula (II) with a compound of formula (III)

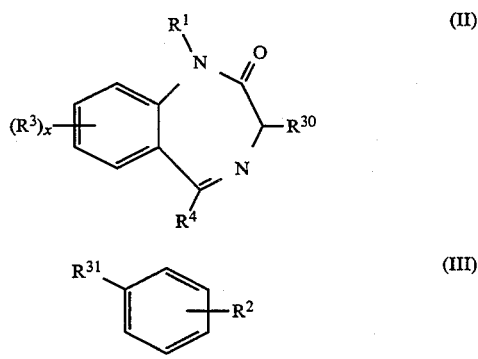

wherein $R^1$, $R^2$, $R^3$, $R^4$ and x are as defined for formula (I), one of $R^{30}$ and $R^{31}$ represents $NH_2$ and the other of $R^{30}$ and $R^{31}$ represents $N=C=O$ or an activated carbamate.

When one of $R^{30}$ and $R^{31}$ represents $N=C=O$, the reaction is preferably conducted in a suitable organic solvent, such as an ether, for example, tetrahydrofuran, at room temperature.

When one of $R^{30}$ and $R^{31}$ represents an activated carbamate the reaction is effected in the presence of a base. Suitable bases for use in the reaction include tertiary amines, for example, triethylamine. Preferably $R^{30}$ represents an activated carbamate and $R^{-}$ represents $NH_2$.

The activated carbamate will suitably be an appropriately substituted aryl carbamate, for example

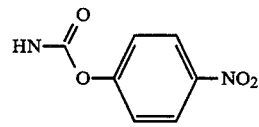

The reaction is conveniently effected in a suitable organic solvent, for example, dimethylformamide, at ambient or elevated temperature. Preferably the reaction is conducted at approximately 50° C.

Intermediates of formula (II) wherein $R^{30}$ is $N=C=O$ (IIB) may be prepared from corresponding amines of formula (II) wherein $R^{30}$ is $NH_2$ (IIA) by conventional methods, for example, by treatment with triphosgene.

Intermediates of formula (II) where $R^{30}$ is an activated carbamate (IIC) may be prepared from compounds of formula (IIA) by reaction with a suitable chloroformate, for example

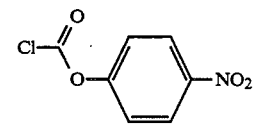

in the presence of a base, such as a tertiary amine, for example, triethylamine.

Intermediates of formula (IIA) may be prepared from compounds of formula (VI)

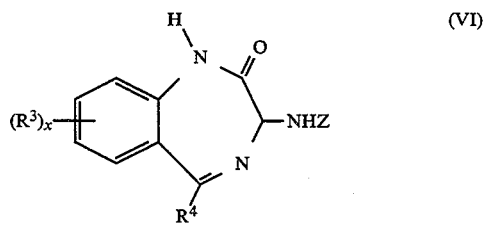

wherein $R^3$, $R^4$ and x are is as defined for formula (I) and Z is a protecting group; by reaction with a reagent suitable to introduce the group $R^1$, for example a halide of formula R1Hal where Hal represents halo such as bromo or iodo, in the presence of a base, such as an alkali metal hydride or an alkaline earth metal carbonate, for example sodium hydride or caesium carbonate; or a suitable dialkyl acetal of dimethyl formamide in a suitable organic solvent, e.g. toluene followed by deprotection.

Compounds of formula (VI) may be prepared from compounds of formula (VII)

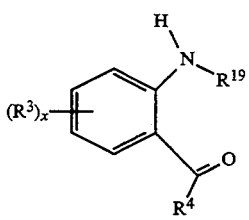

(VII)

wherein $R^3$, $R^4$ and x are is as defined for formula (I) and $R^{19}$ is H, by a reaction sequence comprising:

(i) reaction with a compound of formula (VIII)

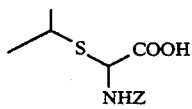

(VIII)

wherein Z is as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC) or isobutyl chloroformate;

(ii) Treatment with gaseous ammonia, preferably in the presence of a mercury containing catalyst, such as mercury (II) chloride. The reaction is conveniently effected in a suitable organic solvent, such as an ether, for example, tetrahydrofuran;

(iii) Treatment with an organic acid, for example acetic or propionic acid, optionally in the presence of an ammonium salt, for example ammonium acetate.

Compounds of formula (VII) wherein $R^{19}$ is H may be prepared from corresponding compounds of formula (VII) wherein $R^{19}$ is $COCH_3$ by treatment with a mineral acid, for example hydrochloric acid, or base hydrolysis, for example, using aqueous sodium hydroxide. The reaction is conveniently affected in refluxing methanol.

Compounds of formula (VII) wherein $R^{19}$ is $COCH_3$ may be prepared from compounds of formula (IX)

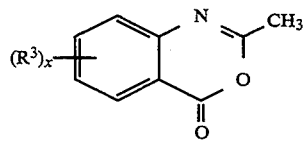

(IX)

wherein $R^3$ and x defined as for formula (I), by reaction with a Grignard reagent of formula $R^4MgHal$ wherein Hal is halo such as chloro, bromo or iodo.

Compounds of formula (IX) may be prepared by known methods, e.g. see D. A. Walsh, Synthesis, 677, (1980).

Alternatively, compounds of formula (VII) wherein $R^{19}$ is H may be prepared by reaction of a compound of formula (X)

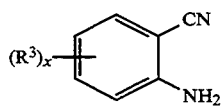

(X)

wherein $R^3$ and x are as previously defined, with a Grignard reagent of formula $R^4MgHal$ wherein $R^4$ is as previously defined and Hal is halo such as chloro, bromo or iodo.

Compounds of formula (X) are commercially available or may be prepared from commercially available compounds by conventional methods.

Intermediates of formula (III) wherein $R^{31}$ represents $N=C=O$ (IIIB) or an activated carbonate (IIIC) may be prepared from the corresponding amines of formula (III) wherein $R^{31}$ is $NH_2$ (IIIA) by conventional methods analogous to those described for the preparation of intermediates of formulae (IIB) and (IIC) from amines of formula (IIA).

Intermediates of formula (IIIA) are known compounds, or may be prepared from the corresponding nitro compounds of formula (XI)

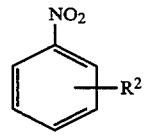

(XI)

wherein $R^2$ is as defined for formula (I), by reduction.

Suitably the reduction is effected by catalytic hydrogen, for example, using a noble metal catalyst such as palladium which may be supported, e.g. on carbon. The reaction is conveniently effected in a suitable organic solvent, such as an alcohol, e.g. ethanol.

Compounds of formula (XI) are commercially available or may be prepared by conventional procedures which will be readily apparent to one skilled in the art.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective-Groups in Organic Chemistry*, ed. J. F. W. McOmie, Plenum Press, 1973; and T. W. Greene and P. M. G. Wutts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

Chromatography was performed on silica gel.

EXAMPLE 1

N-[3(R,S)-2,3-Dihydro-1,5-dimethyl-2-oxo-1H-1,4-benzodiazepin-3-yl]N'-[3-tetrazol-5-ylphenyl]urea

Step 1: 5-(3-Nitrophenyl)tetrazole

To a solution of 3-cyanonitrobenzene (20 g, 0.13 mol) in 1-methyl-2-pyrrolidinone (200 mg) was added triethylamine hydrochloride (27.9 g, 0.20 mol) followed by sodium azide (26.4 g, 0.40 mol). The mixture was heated at 160° C. for 1.5 h, then cooled to ambient temperature, poured into ice water (100 mg) and acidified using 5M HCl. The solid which precipitated from the mixture was filtered, washed with water and dried under vacuum at 50° C. to afford the title tetrazole (22.1 g, 86%) as a beige powder, mp 154°–156° C. $^1$H NMR (360 MHz, CDCl$_{13}$) δ 7.59 (1H, t, J=8 Hz), 8.19 (1H, d, J=8 Hz), 8.36 (1H, d, J=8 Hz), 8.86 (1H, s).

Step 2: 5-(3-Aminophenyl)tetrazole, hydrochloride salt

To a solution of 5-(3-nitrophenyl)tetrazole (22 g, 0.12 mol) in ethanol (500 mg) was added 10% palladium on carbon (1.5 g, 7% (w/w)) in hydrochloric acid (23 mg of a 5M solution). The mixture was hydrogenated at 40 psi for 10 min, then the catalyst filtered off and washed with water. The solvents were evaporated in vacuo and the brown solid azeotroped with toluene (4×100 mg). The resulting solid was triturated with hot ethanol to give 5-(3-aminophenyl)tetrazole hydrochloride (16.3 g, 71%) as a beige powder, mp 203°–205° C. $^1$H NMR (360 MHz, D$_2$O) δ 7.63 (1H, d, J=9 Hz), 7.75 (1H, t, J=8 Hz), 8.00 (2H, m).

Step 3: 1,3-Dihydro-5-methyl-3(R,S)-[(benzyloxycarbonyl)-amino]-2H-1,4-benzodiazepin-2-one @-(Isopropylthio)-N-(benzyloxycarbonyl)glycine (36 g, 0.127 mol) was dissolved in dichloromethane (1000 mg) and cooled to 0° C. The stirred solution was then treated with N-methylmorpholine (13.9 ml, 0.127 mol) followed by isobutyl chloroformate (16.5 ml, 127 mol). The resulting reaction mixture was stirred for a further 15 min at 0° C., then heated to reflux. The refluxing reaction mixture was treated dropwise, over 20 min, with a solution of 2-aminoacetophenone (15 g, 0.11 mol) in dichloromethane (154 ml). After addition was complete the reaction was stirred at ambient temperature for 16 h. The mixture was then washed in succession with 10% o citric acid solution (2×50 ml), saturated sodium bicarbonate solution (2×500 ml) and brine (500 ml). The dried (MgSO$_4$) organic phase was evaporated to afford the crude product as a yellow oil, which was used without further purification. The crude (isopropylthio)glycinamide was dissolved in anhydrous tetrahydrofuran (800 ml) and cooled to 0° C. Ammonia gas was bubbled through the stirred solution for 30 min before addition of mereuric chloride (36 g, 0.132 mol) in one portion. Ammonia was continually bubbled through the solution for a further 2 h, then the suspended solids were filtered off. The solvent was evaporated in vacuo to leave an oil, which was used without further purification.

The crude @-aminoglycinamide was dissolved in glacial acetic acid (500 ml) and treated with ammonium acetate (40 g, 0.52 mol). The resulting reaction mixture was stirred at room temperature overnight, before removing the solvent in vacuo. The residue was partitioned between ethyl acetate (300 ml) and 1N sodium hydroxide solution (300 ml). The organic phase was separated, dried (MgSO$_4$) and evaporated. The residue was chromatographed on silica, using 1:1 petrol:ethyl acetate as eluent to afford 1,3-dihydro-5-methyl-3(R,S)-[(benzyloxycarbonyl)-amino]-2H- 1,4-benzodiazepin-2-one (7.6 g, 21%) as a colourless solid. $^1$H NMR (360 MHz, CDCl$_3$) δ 2.47 (3H, s), 5.05–5.25 (3H, m), 6.50 (1H, d, J=8 Hz), 7.0–7.7 (9H, m), 8.7 (1H, s).

Step 4: 1,3-Dihydro-1,5-dimethyl-3(R,S)[-(benzyl oxycarbonyl )-amino]-2H- 1,4-benzodiazepin-2-one A solution of 1,3-dihydro-5-methyl-3(R,S)[-(benzyloxycarbonyl )-amino]-2H- 1,4-benzodiazepin-2-one ( 2 g, 6.2 mmol) in dimethylformamide (20 ml), under an atmosphere of nitrogen, was treated with sodium hydride (0.26 g of a 57% dispersion in mineral oil, 6.2 mmol) in one portion, at −10° C. After 30 min, iodomethane (0.39 ml, 6.2 mmol) was added and the resulting mixture stirred at room temperature for 3 h. The solvent was then evaporated and the crude residue partitioned between water (20 ml) and dichloromethane (3×20 ml). The combined organic phase was washed with brine (20 ml), dried (MgSO$_4$) and evaporated. The residue was triturated with ether to afford the title compound (1.05 g, 50%) as a colourless solid. $^1$H NMR (360 MHz, CDCl$_3$) δ 2.52 (3H, s), 3.42 (3H, s), 5.0–5.25 (3H, m), 6.65 (1H, d, J=8 Hz), 7.2–7.7 (9H, m).

Step 5: N-[3(R,S)-2,3-Dihydro-1,5-dimethyl-2-oxo-1H-1,4-benzodiazepin-3-yl]N'-[3-tetrazol-5-ylphenyl]urea 1,3-Dihydro-1,5-dimethyl-3(R,S)-[(benzyloxycarbonyl)amino]-2H- 1,4-benzodiazepin-2-one (0.6 g, 1.78 mmol) was dissolved in formic acid/methanol (104 ml of a 4.5% (v/v) solution), and added to a stirred suspension of 10% palladium on carbon (0.22 g) in formic acid methanol (22 ml of a 4.5% (v/v) solution). After 45 min the catalyst was removed by filtration, the filtrate evaporated and the residue partitioned between 10% sodium carbonate solution (20 ml) and dichloromethane (3×20 ml). The combined organic phase was dried (Na$_2$SO$_4$) and evaporated to give a clear oil, which was used without further purification.

To a suspension of 5-(3-aminophenyl)tetrazole hydrochloride (0.274 g, 1.4 mmol) in tetrahydrofuran (10 ml) was added triethylamine (0.38 ml, 2.8 mmol). The mixture was cooled to 0° C., triphosgene (0.13 g, 0.43 mmol) added and adjusted to pH8 by the addition of triethylamine (0.24 ml, 1.76 mmol). The ice bath was removed and the mixture stirred at room temperature for 30 min. A solution of the aminobenzodiazepine (0.217 g, 1.06 mmol), from the above procedure, in tetrahydrofuran (15 ml) was added dropwise to the mixture. The reaction mixture was lo stirred at room temperature for 2 h, then diluted with ethyl acetate (20 ml) followed by 20% aqueous acetic acid (20 ml). After stirring for a further 15 min a colourless precipitate was filtered off. The solid was triturated with ether and then hot methanol to afford the desired material (73 mg, 18%) as a colourless solid, mp 208–210° C. $^1$H NMR (360 MHz, D$_6$-DMSO) δ 2.42 (3H, s), 3.35 (3H, s), 5.15 (1H, d, J=8 Hz), 7.3–7.85 (8H, m), 8.2 (1H, s), 9.25 (1H, s).

EXAMPLE 2

N-[3(R,S)-2,3-Dihydro-1-(2-methylpropyl)-2-oxo-5-(2-propyl) -1H-
1,4-benzodiazepin-3-yl]N'-[3-tetrazol-5-ylphenyl]urea

Step 1: 1,3-Dihydro-5-(2-propyl)-3(R,S) -[(benzyloxycarbonyl)-amino]-2H- 1,4-benzodiazepin-2-one @-(Isopropylthio)-N-(benzyloxycarbonyl)glycine (8.7 g, 30.7 mmol) was dissolved in dichloromethane (130 ml) and cooled to 0° C. The stirred solution was then treated with N-methylmorpholine (3.4 ml, 30.7 mmol) followed by isobutylchloroformate (4.0 ml, 30.7 mmol). The resulting reaction mixture was stirred for a further 15 min at 0° C., then heated to reflux. The refluxing reaction mixture was treated dropwise, over 20 min, with a solution of 1-(3-aminophenyl)-2-methyl-propan-1-one (5 g, 30.7 mmol; ref: Synthesis 1991, p 56) in dichloromethane (50 ml). After addition was complete the reaction was stirred at reflux for 2 h. The mixture was then washed in succession with. 10% citric acid solution (2×100 ml), saturated sodium bicarbonate solution (2×100 ml) and brine (100 ml). The dried (MgSO$_4$) organic phase was evaporated to afford the crude product as a yellow oil which was used without further purification.

The crude (isopropylthio)glycinamide was dissolved in anhydrous tetrahydrofuran (500 ml) and cooled to 0° C. Ammonia gas was bubbled through the stirred solution for 30 min before addition of mercuric chloride (12.5 g, 46mmol) in one portion. Ammonia was continually bubbled through the stirred solution for a further 4 h, then the suspended solids were filtered off. The solvent was evaporated in vacuo to leave an oil, which was used without further purification.

The crude @-aminoglycinamide was dissolved in glacial acetic acid (200 ml) and treated with ammonium acetate (11.1 g, 0.14 mol). The resulting mixture was stirred at room temperature overnight before removing the solvent in vacuo. The residue was partitioned between ethyl acetate (100 ml) and 1N sodium hydroxide solution (100 ml). The organic phase was separated, dried (MgSO$_4$) and evaporated. The residue was chromatographed on silica using 1:1 petrol:ethyl acetate as eluent to afford 1,3-dihydro-5-(2-propyl)-3(R,S) -[(benzyloxycarbonyl)-amino]-2H- 1,4-benzodiazepin-2-one (530 ml, 5%) as a colourless solid. $^1$H NMR (250 MHz, D$_6$-DMSO) δ 0.90 (6H, d, J=7 Hz), 3.14 (1H, m), 5.10 (3H, m), 6.52 (1H, d, J=10 Hz), 7.0–7.6 (9H, m), 9.50 (1H, brs).

Step 2: 1,3-Dihydro-1-(2-methylpropyl)-5-(2-propyl)-3(R,S) -[(benzyloxycarbonyl)-amino]-2H-1,4-benzodiazepin-2-one A solution of 1,3-dihydro-5-(2-propyl)-3(R,S)-[(benzyloxycarbonyl)-amino]-2H-1,4-benzodiazepin-2-one (500 mg, 1.42 mmol) in dimethylformamide (10 ml) under an atmosphere of nitrogen, was treated with sodium hydride (57 mg of a 57% dispersion in mineral oil, 1.42 mmol) in one portion at 0° C. After 1 h, 2-methylpropyl iodide (0.17 ml, 1.50 mmol) was added and the resulting mixture was stirred at room temperature for 16 h. The solvent was then evaporated and the crude residue partitioned between water (15 ml) and dichloromethane (2×20 ml). The combined organic phase was washed with brine (20 ml), dried (MgSO$_4$) and evaporated. The residue was chromatographed on silica using 1:3 ethyl acetate:petrol as eluent, to afford 1,3-dihydro-1-(2-methylpropyl)-5-(2-propyl) -3(R,S)-[(benzyloxycarbonyl)-amino]-2H-1,4-benzodiazepin-2-one (530 mg, 92%) as a colourless solid. $^1$H NMR (250 MHz, CDCl$_3$) δ 0.72 (3H, d, J=8 Hz), 0.80 (3H, d, J =8 Hz), 1.02 (3H, d, J=7 Hz), 1.30 (3H, d, J=7 Hz), 1.64 (1H, m), 3.10 (1H, m), 3.42 (1H, dd, J=15 Hz, 5 Hz), 4.30 (1H, dd, J=12.5 Hz, J=7.5 Hz), 5.12 (3H, m), 6.55 (1H, d, J=10 Hz), 7.10–7.70 (9H, m).

Step 3: N-[3(R,S)-2,3-Dihydro-1-(2-methylpropyl)-2-oxo-5-(2-propyl) -1H-1,4-benzodiazepin-3-yl]N'-[3-tetrazol-5ylphenyl-]urea 1,3-Dihydro-1-( 2-methylpropyl)-5-( 2-propyl)-3(R,S) -[(benzyloxycarbonyl)-amino]-2H-1,4-benzodiazepin-2-one (500 mg, 1.23 mmol) was dissolved in formic acid/methanol (25 ml of a 4.5% (v/v) solution), and added to a stirred suspension of 10% palladium on carbon (100 mg) in formic acid/methanol (25 ml of a 4.5% (v/v) solution). After 30 min the catalyst was removed by filtration, the filtrate evaporated and the residue partitioned between 10% sodium carbonate solution (20 ml) and dichloromethane (3×20 ml). The combined organic phase was dried (Na$_2$SO$_4$) and evaporated to give a clear oil which was used without further purification.

To a suspension of 5-(3-aminophenyl)tetrazole hydrochloride (Example 1, Step 2, 316 ml, 1.6 mmol) in tetrahydrofuran (10 ml) was added triethylamine (0.44 ml, 3.2 mmol). The mixture was cooled to 0° C., triphosgene (157 mg, 0.53 mmol) added and adjusted to pH8 by the addition of triethylamine (0.22 ml, 1.6 mmol). The ice-bath was removed and the mixture was stirred at room temperature for 30 min. A solution of the aminobenzodiazepine (355 mg, 1.2 mmol), from the above procedure, in tetrahydrofuran (10 ml) was added dropwise to the mixture. The reaction mixture was stirred at room temperature for 2 h, then diluted with ethyl acetate (20 ml) followed by 20% aqueous acetic acid (20 ml). The organic phase was separated, dried (Na$_2$SO4) and evaporated. Purification was achieved by preparative HPLC, on a C-18 column with CH$_3$CN:H$_2$O:-HOAc 50:49:1 as eluent affording the product as a colourless solid.ret. time 10 min, mp=220° C. dec. (80 mg, 14%). $^1$H NMR (360 MHz, D$_6$-DMSO) δ 0.64 (3H, d, J=7 Hz), 0.76 (3H, d, J=7 Hz), 0.92 (3H, d, J=8 Hz), 1.20 (3H, d, J=6 Hz), 1.49 (1H, m), 3.33 (1H, m), 3.64 (1H, dd, J=15 Hz, 5 Hz), 4.16 (1H, dd, J=12 Hz, 7 Hz), 5.07 (1H, d, J=8 Hz), 7.20–7.80 (8H, m), 8.13 (1H, s), 9.22 (1H, s).

EXAMPLE 3

N-[3(R,S)-2,3-Dihydro-5-(1,1-dimethylethyl)-1-(2-methylpropyl)
-2-oxo-1H-1,4-benzodiazepin-3yl]N'-(3-(methylsulphonylaminocarbonyl)phenyl]urea

Step 1: 1-(Methylsulphonylaminocarbonyl)-3-nitrobenzene

A solution of methylsulphonamide (5.37 g, 57 mmol) in anhydrous dichloromethane (100 ml), cooled to 0° C. was treated with triethylamine (7.9 ml, 57 mmol) followed by a solution of 3-nitrobenzoyl chloride (10 g, 54 mmol) in anhydrous dichloromethane (100 ml) dropwise. After stirring for 2 h at 0° C., the reaction mixture was washed with 1M HCl (100 ml). The precipitate which formed was collected by filtration and triturated with diethyl ether and was then recrystallised from hot methanol to afford the title compound (4.3 g, 31%) as a colourless crystalline solid, mp 175°–178° C. ¹H NMR (360 MHz, D₆-DMSO) δ 3.42 (3H, s), 7.82 (1H, dd, J=8.0 and 8.0 Hz), 8.38 (1H, d, J=8.0 Hz), 8.49 (1H, d, J=8.0 Hz), 8.80 (1H, s).

Step 2:
1-(Methylsulphonylaminocarbonyl)-3-aminobenzene

To a suspension of 1-(methylsulphonylaminocarbonyl)-3-nitrobenzene (4 g, 16 mmol) in ethanol (100 ml) was added 10% palladium on carbon (0.5 g, 12.5% (w/w)) in water (5 ml). The mixture was hydrogenated at 40 psi for 10 min then the catalyst was filtered off and washed with ethanol. The solvent was evaporated in vacuo to give the title compound (2.9 g, 83%) as a tan powder after trituration with diethyl ether, mp 153°–155° C. ¹H NMR (360 MHz, D₆-DMSO) δ 3.3 (3H, s), 6.79 (1H, d, J=7.7 Hz), 7.05 (1H, d, J=7.7 Hz), 7.08 (1H, d, J=1.9 Hz), 7.13 (1H, dd, J=7.7 and 7.7 Hz).

Step 3: 1-(2-Aminophenyl)-2,2-dimethylpropan-1-one

To a solution of 1-(2-nitrophenyl)-2,2-dimethylpropan-1-one (5 g, 24 mmol) (ref: Aus. J. Chem., 34, 1875–8 (1981)) in ethanol (100 ml) was added 10% palladium on carbon (0.5 g, 10% (w/w)) in hydrochloric acid (5 ml of a 5M solution). The mixture was hydrogenated at 25 psi for 20 min, then the catalyst was filtered off and washed with methanol. The solvents were evaporated in vacuo. The oily residue was partitioned between ethyl acetate (100 ml) and saturated sodium bicarbonate solution (50 ml). The organic phase was separated, washed with brine (25 ml), dried (Na₂SO₄) and evaporated. Trituration of the solid with diethyl ether afforded the title compound as a colourless solid (3 g, 70%). ¹H NMR (250 MHz, CDCl₃) δ 1.38 (9H, s), 5.64 (2H, brs), 6.60–7.30 (4H, m).

Step 4:
1,3-Dihydro-5-(1,1-dimethylethyl)-3(R,S)-[(benzylcarbonyl)-amino]-2H-1,4-benzodiazepin-2-one @-(Isopropylthio )-N-(benzyloxycarbonyl)glycine (1.67 g, 6.5 mmol) was dissolved in dichloromethane (100 ml) and cooled to 0° C. The stirred solution was then treated with N-methylmorpholine (0.71 ml, 6.5 mmol) followed by isobutylchloroformate (0.84 ml, 6.5 mmol). The resulting reaction mixture was stirred for a further 15 min at 0° C., then heated to reflux. The refluxing reaction mixture was then treated dropwise, over 15 min, with a solution of 1-(2'-aminophenyl)-2,2-dimethylpropan-1-one (1.1 g, 6.2 mmol) in dichloromethane (20 ml). After addition was complete the reaction was stirred at reflux for 3 h. The mixture was then washed in succession with 1.0N citric acid (2×25 ml), saturated sodium bicarbonate solution (2×25 ml) and brine (50 ml). The dried (MgSO₄) organic phase was evaporated to afford the crude product as a yellow solid, which was used without further purification.

The crude (isopropylthio)glycinamide was dissolved in anhydrous tetrahydrofuran (120 ml) and cooled to 0° C. Ammonia gas was bubbled through the stirred solution for 30 min before addition of mercuric chloride (2.5 g, 9.3 mmol) in one portion. Ammonia was continually bubbled through the stirred solution for 2 hours, then the suspended solids were filtered off. The solvent was evaporated in vacuo to leave an oil, which was used without purification.

The crude @-aminoglycinamide was dissolved in glacial acetic acid (100 ml) and treated with ammonium acetate (2.3 g, 30 mmol). The resulting mixture was stirred at room temperature overnight, before removing the solvent in vacuo. The residue was partitioned between ethyl acetate (100 ml) and 1.0N sodium hydroxide solution (100 ml). The organic phase was separated, dried (MgSO₄) and evaporated. The residue was chromatographed on silica, using 2:1 petrol:ethyl acetate as eluent, to afford the title compound as a colourless solid (750 mg, 33%). ¹H NMR (250 MHz, D₆-DMSO) δ 1.00 (9H, s), 4.84–4.86 (1H, m), 5.04 (2H, s), 7.10–7.56 (7H, m), 7.75 (1H, d, J=8 Hz), 8.20 (1H, d, J=7 Hz).

Step 5:
-1,3-Dihydro-5-(1,1-dimethylethyl)1-(2-Methylpropyl)-3(R,S)-[(benzyloxycarbonyl)-amino]-2H-1,4benzodiazepin-2-one A solution of 1,3-dihydro-5-(1,1-dimethylethyl)-3(R,S) -[(benzyloxycarbonyl)-amino]-2H-1,4-benzodiazepin-2-one (500 mg, 1.4 mmol) in dimethylformamide (10 ml) under an atmosphere of nitrogen, was treated with sodium hydride (54 mg of a 57% dispersion in mineral oil, 1.4 mol) in one portion at 0° C. After 1 h, 2-methylpropyl iodide (0.17 ml, 1.45 mmol) was added and the resulting mixture stirred at room temperature for 16 h. The solvent was then evaporated and the crude residue partitioned between water (15 ml) and dichloromethane (2×20 ml). The combined organic phases were washed with brine (2×20 ml), dried (MgSO₄) and evaporated. The residue was chromatographed on silica using 2:1 petrol:ethyl acetate as eluent, to afford the title compound as a colourless solid (320 mg, 56%). ¹H NMR (250 MHz, D₆-DMSO) δ 0.63 (3H, d, J=7 Hz), 0.77 (3H, d, J=7 Hz), 1.26 (9H, s), 1.49 (1H, m), 3.56 (1H, dd, J=4 Hz, 14 Hz), 4.10 (1H, dd, J=4 Hz, 14 Hz), 4.88 (1H, m), 5.02 (2H, m), 7.20–7.40 (5H, m), 7.58 (1H, t, J=8 Hz), 7.66 (1H, d, J=9 Hz), 7.77 (1H, d, J=8 Hz), 8.18 (1H, d, J=9 Hz).

Step 6:
1,3-Dihydro-5-(1,1-dimethylethyl)-1-(2-methylpropyl)-3(R,S),[(4-nitrophenyloxycarbonyl)amino]-2H-1,4-benzodiazepin-2-one 1,3-Dihydro-5-(1,1-dimethylethyl)-1-(2-methylpropyl) -3(R,S)-[(benzyloxycarbonyl)amino]-2H-1,4-benzodiazepin-2-one (400 mg, 0.95 mmol) was dissolved in formic acid/methanol (13 ml of a 4.5% (v/v) solution), and added to a stirred suspension of 10% palladium on carbon (50 mg, 12.5% (w/w)) in formic lo acid/methanol (12 ml of a 4.5% (v/v) solution)). After 30 min the catalyst was removed by filtration, the filtrate evaporated and the residue partitioned between 10% sodium carbonate solution (20 ml) and dichloromethane (3×20 ml). The combined organic phase was dried (Na₂SO₄) and evaporated to give a colourless solid, which was used without further purification.

A solution of the crude 3(R,S)-amino-1,3-dihydro-5-(1,1-dimethylethyl)-1-(2-methylpropyl)-2H-1,4-benzodiazepin-2one (200 ml, 0.7 mol) in dry THF (15 ml) under an atmosphere of nitrogen at 0° C. was treated with triethylamine (0.10 ml, 0.7 mol) followed by a solution of 4-nitrophenylchloroformate (141 mg, 0.7 mmol) in THF (15 ml). After stirring at room temperature for 20 min the solid which precipitated was removed by filtration and the filtrate concentrated in vacuo to afford 160 mg (51% yield) of the titled compound as a colourless solid. $^1$H NMR (360 MHz, CDCl$_3$) δ 0.76 (3H, d, J=7 Hz), 0.84 (3H, d, J=7 Hz), 1.34 (9H, s), 1.69 (1H, m), 4.31 (1H, m), 5.11 (1H, d, J=8 Hz), 6.64 (1H, d, J=8 Hz), 7.20–7.60 (5H, m), 7.70 (1H, m), 8.22 (2H, m).

Step 7:
N[3(R,S),2,3-Dihydro-5-(1,1-dimethylethyl)-1-(2-methylpropyl)-2-oxo-1H-1,4-benzodiazepin-3-yl]N'-[3-(methylsulphonylaminocarbonyl)phenyl]urea A solution of-1,3-dihydro-5-(1,1-dimethylethyl)-1-(2-methylpropyl) -3(R,S)-[(4-nitrophenyloxycarbonyl)amino]-2H-1,4-benzodiazepin-2-one (140 ml, 0.3 mol) in anhydrous dimethylformamide (3 ml) under an atmosphere of nitrogen was treated with triethylamine (0.043 ml, 0.3 mol) and stirred at ambient temperature for 5 min. To the reaction mixture was added dropwise a solution of 1-(methylsulphonylaminocarbonyl)-3-aminobenzene (66 mg, 0.3 mmol) in anhydrous dimethylformamide (3 ml). The reaction was stirred at 50° C. for 3.5 h. The solvent was evaporated in vacuo and the residue partitioned between ethyl acetate (15 ml) and aqueous acetic acid (20%, 5 ml). The layers were separated and the aqueous phase washed with ethyl acetate (2×15 ml). The combined organics were dried (MgSO$_4$), evaporated and triturated with ether to give a beige solid. The crude product was recrystallised from methanol to afford the title compound as a colourless solid (60 mg, 38%) mp=250° C. (dec.). $^1$H NMR (360 MHz, D$_6$-DMSO) δ 0.65 (3H, d, J=7 Hz), 0.79 (3H, d, J=7 Hz), 1.26 (9H, s), 1.51 (1H, m), MeSO$_2$ peak, 3.35 (3H, s), 3.59 (1H, m), 4.13 (1H, m), 5.03 (1H, m), 7.30–8.00 (9H, m), 9.16 (1H, s), 12.08 (1H, s).

EXAMPLE 4A Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 4B Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 5 Parenteral insection

|  | Amount mg |
| --- | --- |
| Compound of formula (I) | 1 to 100 |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 6 Topical formulation

|  | Amount mg |
| --- | --- |
| Compound of formula (I) | 1–10 |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mM N-2-hydroxyethyl-piperazine-N'-2-ethane sulphonic acid (HEPES) buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20 mM (HEPES)), 1 mM ethylene glycol-bis-(β-aminoethylether-N,N'-tetraacetic acid) (EGTA), 5 mM MgCl$_2$, 150 mM NaCl, bacitracin 0.25 ml/ml, soya bean trypsin inhibitor 0.1 ml/ml, and bovine serum albumin 2 ml/ml pH 6.5 at 25° C.) using a Teflon (trademark) homogenizer, 15 strokes at 500 rpm. The homogenate was further diluted in binding assay buffer to give a final concentration of 0.5 ml original wet weight/1 ml buffer. For the binding assay, 50 μl of buffer (for total binding) or unlabelled CCK-8 sulphated to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. 50 pM final concentration) were added to 400 μl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 Mm NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The $P_2$ pellet was resuspended in binding assay buffer (20 mM HEPES, 5 mMMgCl$_2$, 0.25 ml/ml bacitracin, 1 mM EGTA pH 6.5 at 25° C.), using a Teflon (trademark) homogenizer (5 strokes at 500 rpm) to give a final concentration of 10 ml original wet weight/1.2 ml buffer. For the binding assay, 50 μl of buffer (for total binding) or unlabelled CCK-8 sulphated to give a final concentration of 1 μM (for non-specific binding) or the compounds of Formula I (for determination of inhibition of $^{125}$I-CCK-8 binding) and 50 μl of 500 pM $^{125}$I-CCK-8 (i.e. final concentration of 50 pM) were added to 400 μl of the membrane suspensions in microfuge tubes. All assays were run in duplicate. The reaction mixtures were incubated at 25° C. for 2 hours and then the reaction was terminated by rapid filtration (Brandell 24 well cell harvester) on Whatman GF/C filters with 3×5 ml washes of cold 100 mM NaCl. The radioactivity on the filters was counted with a LKB gamma counter.

In Vitro Results

Effects of the Compounds of Formula I on $^{125}$I-CCK-8 receptor binding

The preferred compounds of Formula I are those which produced dose-dependent inhibition of specific $^{125}$I-CCK-8 binding as defined as the difference between total and non-specific (i.e. in the presence of 1 μM CCK) binding.

Drug displacement studies were performed with at least 10 concentrations of compounds of Formula I and the IC$_{50}$ values were determined by regression analysis IC$_{50}$ refers to the concentration of the compound required to inhibit 50% of specific binding of $^{125}$I-CCK-8.

The data in Table I were obtained for compounds of Formula I.

TABLE I

| CCK RECEPTOR BINDING RESULTS IC$_{50}$ (nM) | | |
|---|---|---|
| Compound of Ex # | $^{125}$I-CCK Pancreas | $^{125}$I-CCK Brain |
| 1 | >3000 | 104 |
| 2 | 600 | 17 |
| 3 | 612 | 32 |

We claim:

1. A compound of formula (I):

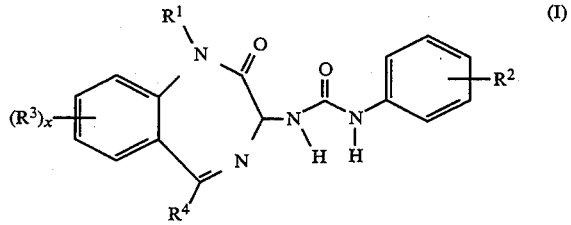

wherein

R$^1$ is selected from H, C$_{1-6}$ alkyl, C$_{3-7}$ cycloalkyl, cyclopropylmethyl, CH$_2$CO$_2$R$^5$, where R$^5$ is C$_{1-4}$ alkyl and CH$_2$CONR$^6$R$^7$, where R$^6$ and R$^7$ are each independently selected from H and C$_{1-4}$ alkyl, or R$^6$ and R$^7$ together form a chain (CH$_2$)$_p$ where p is 4 or 5;

R$^2$ is selected from (CH$_2$)$_q$-tetrazolyl, (CH$_2$)$_q$- tetrazolyl substituted in the tetrazole ring by C1–4 alkyl, (CH$_2$)$_q$- imidazolyl, where q is 0, 1, 2, or 3, CONHSO$_2$R$^9$, SO$_2$NHCOR$^9$, where R$^9$ is selected from C$_{1-6}$ alkyl, unsubstituted aryl, substituted aryl, wherein said aryl can be substituted with C$_{1-4}$ alkyl, C$_{1-4}$ alkoxy, halo or trifluoromethyl; and, SO$_2$NHR$^{10}$, where R$^{10}$ is a nitrogen containing heterocycle, selected from thiazole, thiadiazole, or pyrazine;

R$^3$ represents C$_{1-6}$ alkyl, halo or NR$^{16}$R$^{17}$, where R$^{16}$ and R$^{17}$ each independently represent H or C$_{1-4}$ alkyl, or R$^{16}$ and R$^{17}$ together form a chain (CH$_2$)$_r$ where r is 4 or 5;

R$^4$ represents C$_{1-7}$ straight or branched chain alkyl;

x is selected from 0, 1, 2 and 3;

or a pharmaceutically acceptable salt or pharmaceutically acceptable prodrug thereof.

2. A compound as claimed in claim 1 wherein R$^2$ is selected from CONHSO$_2$R$^9$ and SO$_2$NHCOR$^9$.

3. A compound as claimed in claim 1 wherein R$^2$ represents tetrazolyl.

4. A compound as claimed in claim 1 wherein R$^1$ represents C$_{1-6}$alkyl.

5. A compound as claimed in claim 1 selected from:
N-[3(R,S)-2,3-dihydro-1-(2-methylpropyl)-2-oxo-5-(2-propyl)-1H-1,4-benzodiazepin-3-yl]N'-[3-tetrazol-5-ylphenyl]urea;
N-[3(R,S)-2,3-dihydro-1,5-dimethyl-2-oxo-1H-1,4-benzodiazepin-3-yl]N'-[3-tetrazol-5-ylphenyl]urea;
N-[3(R,S)-2,3-dihydro-5-(1,1-dimethylethyl)-1-(2-methylpropyl)-2-oxo-1H-1,4-benzodiazepin-3-yl]N'-[3-(methylsulphonyaminocarbonyl) phenylurea;
and salts and prodrugs thereof.

6. A pharmaceutical composition comprising a pharmaceutically effective amount of a compound according to claim 1 in association with a pharmaceutically acceptable carrier or excipient.

7. A method for the treatment or prevention of a physiological disorder involving CCK and/or gastrin, which method comprises administration to a patient in need thereof of a CCK and/or gastrin reducing amount of a compound according to claim 1.

8. A method as claimed in claim 7 for the treatment or prevention of anxiety.

9. A method as claimed in claim 7 for the treatment or prevention of panic.

10. A method as claimed in claim 7 for the treatment of pain.

* * * * *